United States Patent [19]
Wood et al.

[11] 3,963,719
[45] June 15, 1976

[54] 6-SPIROCYCLOALKYLAMINO 5-NITROPYRIMIDINES

[75] Inventors: Hamish Christopher Swan Wood, Bearsden, Scotland; Irene Stirling, Worcester Park, England

[73] Assignee: Burroughs Wellcome Co., Research Triangle Park, N.C.

[22] Filed: July 30, 1973

[21] Appl. No.: 383,698

[30] Foreign Application Priority Data
Aug. 1, 1972 United Kingdom............ 35814/72

[52] U.S. Cl.............. 260/256.4 C; 260/251.5; 260/566 A; 260/647; 424/251
[51] Int. Cl.$^2$...................... C07D 239/22
[58] Field of Search.......................... 260/256.4 C

[56] References Cited
UNITED STATES PATENTS
3,635,978   1/1972   Wood et al. ............ 260/256.4 C X
3,810,893   5/1974   Wood et al. ................ 260/256.4 C

*Primary Examiner*—Richard L. Raymond
*Attorney, Agent, or Firm*—Donald Brown

[57] ABSTRACT

Novel pteridines of formula (I),

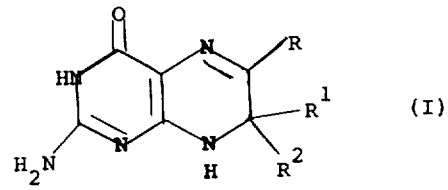

wherein R is a lower alkyl group, optionally substituted with a hydroxy group and $R^1$ and $R^2$ are the same or different and each is a lower alkyl group having together at least 3 carbon atoms or $R^1$ and $R^2$, together with the carbon atom in the pteridine ring structure, form a spirocycloalkyl ring system having 4 to 6 carbon atoms outside the pteridine ring structure, and their method of preparation.

The above compounds have bacteriostatic activity.

2 Claims, No Drawings

6-SPIROCYCLOALKYLAMINO 5-NITROPYRIMIDINES

The present invention relates to derivatives of pteridine, their chemical synthesis and pharmaceutical formulations containing them. The specification also describes compositions and pharmaceutical formulations comprising these pteridines in combinations which are useful in the treatment of microbial infections.

It is already established that the compounds 2-amino-4-hydroxy-6-hydroxymethyl-7,7-dimethyl-7,8-dihydropteridine and 2-amino-4-hydroxy-6-methyl-7,7-dimethyl-7,8-dihydropteridine or their tautomers or pharmaceutically acceptable saltss thereof, have bacteriostatic activity, being particularly effective against *Cl. perfringens* and *Derm. dermatonomous*, as disclosed in the specifications of British Patent No. 1303171 and Application No. 36289/70 (Belgian Patent No. 770,577).

It has now been found that the novel pteridines represented by the following formula (I) or their tautomers or pharmaceutically acceptable salts thereof,

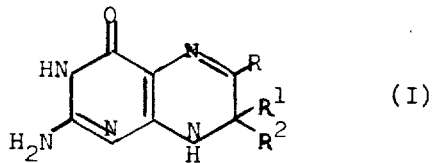

(I)

wherein R is a lower alkyl group, optionally substituted with a hydroxy group, and $R^1$ and $R^2$ are the same or different and each is a lower alkyl group having together at least 3 carbon atoms or $R^1$ and $R^2$, together with the carbon atom in the pteridine ring structure, form a spirocycloalkyl ring system having 4 to 6 carbon atoms outside the pteridine ring structure, are also useful as antagonists of microbial metabolism.

As used herein and throughout the specification, the term "lower alkyl group" refers to a straight or branched chain alkyl group which, unless otherwise specified, has 1 to 4 carbon atoms.

In the above formula, preferred compounds are those wherein R is a hydroxyalkyl group, in particular a hydroxymethyl group. Moreover those compounds wherein $R^1$ and $R^2$, together with the carbon atom in the pteridine ring structure, form a spirocyclohexyl group, or especially those wherein $R^1$ and $R^2$ are both alkyl groups, in particular ethyl groups, are further preferred. Thus the compounds 2-amino-4-hydroxy-6-hydroxymethyl-7,7-diethyl-7,8-dihydropteridine and less preferably 2-amino-4-hydroxy-6-hydroxymethyl-7-spirocyclohexyl-7,8-dihydropteridine have been found to be particularly useful in the treatment of microbial infections.

According to the present invention, therefore, there are provided in one aspect the novel compounds of formula (I).

The above compounds and their salts inhibit one of the enzymes involved in the biosynthesis of dihydrofolic acid, namely hydroxymethyldihydropteridine pyrophosphokinase, which is essential to the growth of microorganisms, for instance bacteria. They can thus be used in in vitro pharmacological investigations in clinical and diagnostic tests establishing, for instance, the properties of bacteria. When used as bacteriostats they may be present in a concentration of 50 to 500, in particular 110 to 180 mg of base/ml of the solution in which the organism grows in the absence of a compound. A further use of the compounds, when in solution, is in the treatment of wounds, for example after surgery, to prevent the growth of bacteria. Moreover the compounds of formula (I) and their salts manifest unexpectedly low toxicity in mammals or birds e.g. poultry, which makes them particularly suitable for application against microbial infections in such hosts under circumstances hereinbelow described.

Tetrahydrofolate co-factors are essential metabolites in all cells for the biosynthesis of purines, thymidylic acid, serine and several other biologically important compounds. Most of these co-factors are onecarbon adducts of tetrahydrofolic acid. The ultimate source of these for higher animals and man is food, containing preformed folates usually in the form of vitamins.

In microorganisms, the co-factors are synthesised from simpler chemicals. Generally the bio-synthetic process first provides 'dihydropteridine' (Pt), i.e. 2-amino-4-hydroxy-6-hydroxymethyl-7, 8-dihydropteridine (HMPt) pyrophosphate ester, from its immediate precursor HMPt in the presence of the enzyme hydroxymethyldihydropteridine pyrophosphokinase (HMPPS). Pt then condenses with p-aminobenzoic acid (pAB) in the presence of the enzyme dihydropteroate synthetase to form dihydropteroic acid (DPtA). This intermediate further condenses with a glutamate to form dihydrofolic acid (DFA or 'folate') which is then enzymatically reduced to provide the essential tetrahydrofolate in, for instance, bacteria and other micro-organisms.

The provision of the 'folate' from the basic building blocks, i.e. pteridine, pAB, and glutamate, and the further conversion of this into the tetrahydrofolate is known to be inhibited in two different ways. For instance sulphonamides displace pAB in the above reaction scheme. Because of their close structural resemblance to pAB, sulphonamides or similar other 'competitors' enter the biosynthesis and prevent the formation of DPtA, and of DFA, and are therefore antimetabolites for the metabolite pAB. It is also known that compounds which are 'inhibitors' of the enzyme dihydrofolic acid reductase block the synthetic step leading to tetrahydrofolate. A considerable number of pyrimidine derivatives show substantial anti-microbial properties on the basis of such blockage.

It was established later that such inhibitors may act synergistically with sulphonamides, i.e. there can be a sequential double blockade and a strong mutual potentiation of the anti-bacterial effects of the two materials. The range of anti-microbial action exerted by such combinations is considerably wider than that expected from the activity of either drug, and organisms which are only marginally sensitive to the individual agents become very sensitive to the combinations.

It was also suggested hypothetically that antimetabolites to Pt could inhibit the biosynthesis of DPtA (and DFA) (cf. Hitchings and Burchall *Advances in Enzymology*, 27, 417–468 (1965)) but compounds so far tested for the purpose have been disappointing, being either inactive or too toxic or sometimes both (cf. the compounds described in British Patent Nos. 981,506 and 987,916).

It has been established that, for antimicrobial purposes, it is a prerequisite for the effective antagonism of Pt that the compound should be an inhibitor of HMPPS without also acting as an antimetabolite to the dihydropteridine that serves as a cofactor for the hydroxylation of phenylalanine and tyrosine, precursors of the catecholamines, such as norepinephrine, that have important actions as regulators of cardiovascular systems. Such an antimetabolic effect could lead to prohibitive toxicity to avian or mammalian species, which are normally the hosts infected with the microbes.

It has now been found that the compounds of formula (I) and their salts fulfil the above requirements i.e. inhibition of HMPPS combined with low toxicity to host species, as demonstrated for instance in chicks and rats. These compounds not only inhibit the growth of microorganisms on their own, albeit to a limited extent with certain bacteria, such as *Staphylococcus aureus*, *Streptococcus pyogenes*, *Streptococcus faecalis*, *Escherichia coli*, *Salmonella typhi*, *Proteus vulgaris*, *Pseudomonas aerugenosa*, *Pasteurella multocida* among others, but have been found to act with a most remarkable synergistic effect when combined with a competitor of p-aminobenzoic acid, i.e. sulphonamides and similar compounds, or with selective inhibitors of dihydrofolic reductase, i.e. pyrimidines and related compounds, or with a combination of both of these types of antimicrobial agents. This potentiating effect of the compounds of formula (I) is the subject of co-pending cognate British Patent Application No. 36774/71.

In that application there is described and claimed a composition for testing or treating microbial systems or infections, comprising an effective potentiating amount of a compound of formula (I) in combination with an effective amount of a competitor or inhibitor, or both, as herein defined.

The microbial infections against which these combinations are effective are protozoal or bacteria infections caused by those microorganisms which synthesise at least a substantial part of their tetrahydrofolate cofactor requirements. More specifically these infecting microorganisms are those which adequately absorb the pharmaceutical combinations disclosed herein and further are those in which these combinations have a synergistic effect in interfering with the de novo synthesis of the required tetrahydrofolate co-factors. For example, the compositions described have been found to be useful in the treatment of infections caused by *Staphylococcus aureus*, *Pseudomonas aerugenosa* and *Pasteurella multocida*.

It has been found specifically that, when compounds of formula (I) are combined with an amount of the competitor and/or the inhibitor which is not ordinarily sufficient to be effective as an antimicrobial agent in its own right, the combination of a compound of formula (I) with this normally ineffective amount of the competitor and/or the inhibitor provides a composition which in totality acts as an effective antimicrobial agent. This is especially notable when the amount of the compound of formula (I) is so low that it has substantially no microbial effect at the particular level, yet in the combination the potentiation is marked, in some instances very marked. Thus by using an effective potentiating amount of a compound of formula (I) together with the competitor and/or the inhibitor, it is now possible to reduce significantly the amount of the competitor and/or the inhibitor required to inhibit the growth of these bacteria.

In accordance with the above therefore, the term "an effective amount" used in conjunction with the terms a dihydrofolic reductase 'inhibitor' and a para-aminobenzoic acid 'competitor' means either (a) an amount of the 'inhibitor' or 'competitor' which is effective to a degree as an antimicrobial agent in its own right but which is potentiated by the use of a compound of formula (I) or (b) an amount of the 'inhibitor' or 'competitor' which is ineffective as an antimicrobial agent by which when combined with a compound of formula (I) provides a composition which is an effective antimicrobial agent. An "effective potentiating amount" means an amount of the compound of formula (I) which increases the activity of an inhibitor and/or a competitor so as to provide an improved or adequate effectiveness for the whole combination.

It should be emphasised that the inhibition of the biosynthetic processes by such means could be termed as competitive antagonism in all three instances, and there might be potentiation between all three types of agents. The terms 'inhibitor', 'competitor', and 'potentiation' by a compound of formula (I) are arbitrary and should only serve as convenient names for the appropriate type of components in combination products described and claimed in the specification of the aforementioned cognate application.

The inhibiting activity against HMPPS of a selected compound of formula (I) can, for instance, be tested by monitoring the transfer of the terminal phosphate of adenosine triphosphate ATP-$\gamma$-$P^{32}$ to 'dihydropteridine'. It was found that the concentrations required for 50% inhibition of the formation of Pt ($IC_{50}$) in such tests are well correlated and within the margin of error obtained by other relevant tests in this respect, which measure the inhibition of either of the two enzymes involved in the formation of HMPt and DPtA. Such inhibition may, for instance, be easily and simply carried out by incubating an extract of E. coli with pAB-7-$C^{14}$, ATP, Mg and 'dihydropteridine'. The formation of the dihydropteroate-$C^{14}$ can be quantitatively assayed after separating the unreacted pAB substrate, for instance by chromatography. It has been found that compounds possessing in such tests an $IC_{50}$ value of about 100$\mu$M, or less, usually below 50$\mu$M represent compounds exerting a useful potentiating effect, provided their toxicity in the appropriate vertebrates is acceptable. Preferably the value is 25$\mu$M or less, such as in the range between 2 to 12$\mu$M. Generally a value below 7$\mu$M is desirable.

As explained above, for the purpose disclosed it is essential that the compound of formula (I) should not have a prohibitive toxicity to the mammalian or avian hosts' cardiovascular systems. While low toxicity is therefore an essential requirement, a therapeutic index incorporates both the activity and toxicity values pertinent to the present disclosure and could be used with advantage for the selection of potentiating compounds of formula (I).

The therapeutic index is defined as the ratio of the maximum tolerated dose to the minimum effective dose and in most cases is preferably greater than 10, suitably at least 5 and in exceptional circumstances at least about 3 for humans, but possibly as low as 2 for animals.

Although the art is aware of many compounds which are known competitors of para-aminobenzoic acid and are antimicrobials, the sulphur compounds which are disclosed as antimicrobial agents from the top of page 994 to page 1007 of the Merck Index, 8th Edition, 1968 are presented by way of example only.

Of the known compounds which are competitors, the following sulphonamide compounds (or pharmaceutically acceptable salts thereof) are preferred for the purpose described.

Sulphanilamide, sulphadiazine, sulphamethisazole, sulphamethizole, sulphapyridine, sulphathiazole, sulphamerazine, sulphamethazine, sulphisoxazole, sulphadoxine, sulphasomidine, sulphachlorpyridazine, 2-(p-aminobenzene)-sulphonamido-3-methoxypyrazine(Kelfizina), α-amino-p-toluenesulphonamide, 5-sulphanilamido-2,4-dimethyl pyrimidine, 4-(N'-acetyl sulphanilamido)-5,6-dimethoxy pyrimidine, 3-sulphanilamido-4,5-dimethyl isoxazole, 4-sulphanilamido-5-methoxy-6-decyloxy pyrimidine, sulphamonomethoxine, 4-p-(8-hydroxy-quinilinyl-4-azo)-phenyl sulphanilamido-5, 6-dimethoxy pyrimidine, sulphadimethoxine, sulphamethoxazole, sulphaquinoxaline, and p-(2 methyl-8-hydroxy-quinolinyl-(5)-azo)-phenyl sulphanilamido-5,6-dimethoxy pyrimidine. Examples of a non-sulphonamide type of competitor are p-amino salicylic acid (PAS) and p,p'-diaminodiphenylsulphone.

Similarly, although many compounds are known which inhibit dihydrofolic reductase and act as antimicrobial agents, the compounds disclosed in the following patents are presented by way of example of compounds suitable for use for the purpose disclosed.

U.S. Pat. Nos. 2,658,897; 2,767,183; 3,021,332; 2,937,284; 3,322,765; 2,909,522: 2,624,732; 2,579,259; 2,945,859; 2,576,939; 2,926,166; 2,697,710; 2,749,345; and 2,749,344.

The following inhibitors (or pharmaceutically acceptable salts thereof) are preferred for the combinations described, however:

2,4-diamino-6-ethyl-5-p-chlorophenylpyrimidine (pyrimethamine), 2,4-diamino-5-(3'4',5'-trimethoxybenzyl)-pyrimidine (trimethoprim), 2,4-diamino-5-(3'4'-dimethoxybenzyl) pyrimidine (diaveridine), 2,4-diamino-5-(2'-isopropyl-4'-chlorophenoxy) pyrimidine, 2,4-diamino-5-methyl-6-sec-butylpyrido (2,3-d) pyrimidine, 2,4-diamino-5-methyl-6-benzylpyrido(2,3-d) pyrimidine, 2,4-diamino-6-benzylpyrido(2,3-d) pyrimidine, 2,4-diamino-5-6-trimethylenequinazoline, 2,4-diamino-5,6-tetramethylenequinazoline, 2,4-diamino-5-(2',4'5'-trimethoxybenzyl) pyrimidine, 2,4-diamino-5-(2'-ethyl-4',5-dimethoxybenzyl) pyrimidine, 2,4-diamino-5-(2'-methyl-4',5'-dimethoxybenzyl) pyrimidine.

However, the most preferred combinations include those combining a compound of formula (I), especially that wherein R is a hydroxymethyl group and $R^1$ and $R^2$ are both ethyl groups, with sulphadiazine, sulphamethoxazole, sulphadoxine or sulphaquinoxaline as competitors, or with trimethoprim, diaveridine or pyrimethamine as inhibitors. In view of possible synergistic advantages of using certain competitors and inhibitors in combination against particular diseases, and the potentiating effect of compounds of formula (I) on both of these types of antibacterial compounds, it has been preferred to formulate triple combinations, comprising a compound of formula (I) with one of the above-mentioned preferred competitors, and one of such inhibitors. For example, combinations of sulphadiazine/trimethoprim, sulphamethoxazole/trimethoprim, sulphadoxine/trimethoprim or sulphaquinoxaline/diaveridine, each together with a compound of formula (I), give improved effectiveness when compared with the components alone or with pairs of them.

The compounds of formula (I) either alone or together with the competitor and/or the inhibitor, may be presented in association with a carrier in pharmaceutical formulations suitable for parenteral, topical, rectal or oral administration. The formulations for oral or rectal administration are advantageously presented in discrete units, such as tablets, capsules, cachets, ampoules or suppositories, each containing a predetermined amount of each compound, but may also be presented as a powder, as granules, as a solution or suspension in an aqueous or non-aqueous liquid, or as an ointment or paste for topical administration. For parenteral use, the formulations incorporating an aqueous or non-aqueous liquid carrier must be sterile and be presented in sealed containers. The formulations may be made by any of the known methods and may include one or more of the following accessory ingredients:

diluents, solutes to render the solution isotonic with the blood, buffers, flavouring, binding, dispersing, surface-active, thickening, lubricating and coating materials, preservatives, bacteriostats, antioxidants, suppository and ointment bases, and any other acceptable excipients.

In another aspect of the present invention, therefore, there is provided a pharmaceutical formulation comprising a compound of formula (I) in combination with a pharmaceutically acceptable carrier. In yet another aspect the present invention provides a method of making a pharmaceutical formulation by admixing the compound of formula (I) with a carrier by known techniques. The specification of the afore-mentioned cognate application further discloses and claims a pharmaceutical formulation comprising a composition, as hereinbefore defined, together with a carrier, and its method of preparation, by admixing the composition with the carrier by known, techniques.

Formulations containing the compound of formula (I) in association with a competitor or an inhibitor may also be presented in the form of a kit, which comprises separately packaged units or dosages of these components with instructions for use in a combined form. The instructions may also specify the manner of administration and indications for which the formula is suitable.

The compounds of formula (I), either for use alone or in association with a competitor and/or inhibitor, and also the competitors and inhibitors, may be presented in the form of their pharmaceutically acceptable salts of a mineral or organic acid, for example hydrochloric acid, hydrobromic acid, sulphuric acid, acetic acid, citric acid, tartaric acid, lactic acid, maleic acid or salicylic acid, or, especially for the sulphonamide competitor, of a base, such as sodium hydroxide, potassium hydroxide, tetramethyl ammonium hydroxide or ammonia.

The ratios in which the therapeutically active compounds of formula (I) are utilized in the compositions described in this specification can be varied between wide limits. Depending on the nature and circumstance of use, the compositions may contain the compound of formula (I) with the competitor and/or the inhibitor in appropriate proportions and dosages. For instance, in cases of uses in vivo it is often desirable to maintain a certain proportion of components in the blood serum or tissue fluids, preferably for a prolonged period. Depending on the various absorption, discharge or decomposition rates of the components, the initial quantities and proportions of the ingredients of the formulation can be different from that aimed at in the tissues in vivo. The formulations and dosages recommended for the general treatment of a particular human or animal disease must be adjusted according to the particular requirements of the recipients of the disease, the known activities of the competitor or inhibitor component against the causative organism, the half life and the toxicity of the components in vivo, and other practical requirements.

For example the composition or pharmaceutical formulation may contain from about 1 to 30 parts by weight, preferably 5 to 15 parts, of the compound of formula (I), or an equivalent amount of a salt thereof, and 1 to 30 parts, preferably 5 to 15 parts, of a competitor, or an equivalent amount of a salt thereof, and/or one part of an inhibitor, or an equivalent amount of a salt thereof.

Dosage will vary depending upon the infecting organism but under ordinary circumstances up to about 60 mg/kg each of a compound of formula (I) and competitor, and up to about 7.5 mg/kg of inhibitor, in combination, can be administered daily in several doses. The composition or pharmaceutical formulation can be administered to human patients in unit dosage forms which contain up to 750 mg of the compound of formula (I), and up to 750 mg of the competitor and/or up to 25 mg of the inhibitor. Preferably for adult dosages the amount of the compound of formula (I) would be about 200 mg, that of the competitor about 200 mg and/or that of the inhibitor about 25 mg.

The pharmaceutical formulation comprising the compound of formula (I) in combination with the competitor and/or the inhibitor is also usable in solution for irrigating wounds, for example after surgery, so as to prevent the growth of bacteria. For example, an antibacterial solution having the following preferred concentration of components may be used:

1–30 mg/ml of the compound of formula (I), 1–30 mg/ml of the competitor and/or 0.03–1 mg/ml of the inhibitor, in a pharmaceutically acceptable solvent, suitable for external use.

The potentiating effect of compounds of formula (I) can be demonstrated and utilized in vitro relatively easily for research and practical purposes. Such possibilities include diagnosis and the identification of the bacterial flora of individuals and the consequential selection of clinical treatment schedules.

The various combinations can be incorporated in porous discs (such as filter paper discs) or in Agar Nutrient or other media for bacterial growth for determining susceptibility. Those articles incorporating the compound of formula (I) with a competitor and/or an inhibitor compound may be distributed or sold to doctors, hospitals and clinics for the above purposes. A typical testing disc may be impregnated with a solution containing 5 to 50 μg/ml of a para-aminobenzoic acid competitor, 0.5 to 5 μg/ml of a dihydrofolic reductase inhibitor, and about 10 to 100 μg/ml of a compound of formula (I) in a medium comprising a mixture of an aqueous infusion and papain digest of horse muscle.

Furthermore, such pharmacological tests involving potentiated competitors or inhibitors may also be useful for the characterisation of bacteria according to their sensitivity and to their particular resistance for instance to a competitor when used alone, and such investigations involving a variety of formulations as described herein also form the basis of determining the compositions of selected formulations for general treatment purposes. The toxicity of compounds of formula (I) is generally considerably lower than that of the competitors or inhibitors commonly used, which may enable the clinician to maintain or increase the effectiveness of the antibacterial activity of the formulation with a concurrent increase of the therapeutic ratio or decrease in the toxic or side-effects of the medicament.

In addition to the above, compounds of formula (I) have been found to potentiate the activity of the aforementioned competitors and/or inhibitors against infections with microorganisms in domestic animals, including poultry, for example against *Pasteurella multocida* but especially against the protozoal disease coccidiosis. Such triple formulations comprising a compound of formula (I) together with a compound such as sulphaquinoxaline and an inhibitor such as diaveridine are effective in lower concentrations than the competitor or inhibitor components alone and possess an enhanced activity, being effective against all relevant Eimeria species causing this disease in poultry.

The compounds of formula (I) may be prepared by the reductive cyclisation of a compound of formula (II),

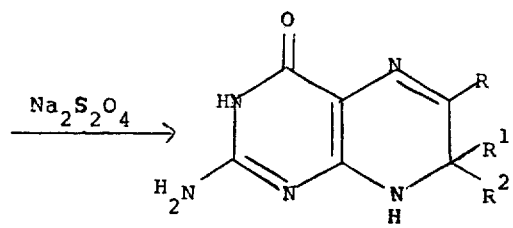

(I)

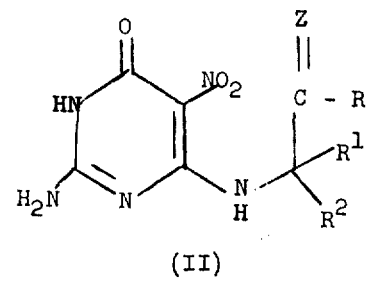

(II)

wherein R, R¹ and R² are as defined above and Z is a ketonic oxygen atom or a protecting group therefor, such as a semicarbazone group or an oxime group, prepared according to the procedures diclosed by Pfleiderer and Zondler (*Chem. Ber.* 99, 3008 (1966)) and the specifications of British Patent No. 1303171 and of co-pending Bristish Patent Application No. 36289/70 (Belgian Patent No. 770,577) respectively.

The method described in British Patent Application No. 36289/70, however, is particularly preferred.

In this method, a compound $R^1R^2C = CHR$ (VI), wherein R, R¹ and R² are as defined above, undergoes an addition reaction with a nitrosyl halide, prepared in situ, and the resulting nitrosohalide (V) is converted to the oxime (IV) by reaction with ammonia solution. Reacting the oxime (IV) with a 2-amino-4-halogeno-6-hydroxy-5-nitropyrimidine (III) provides the pyrimidine ketoxime (II) which is then reductively cyclised to give the pteridine (I), as shown in the following sequence:

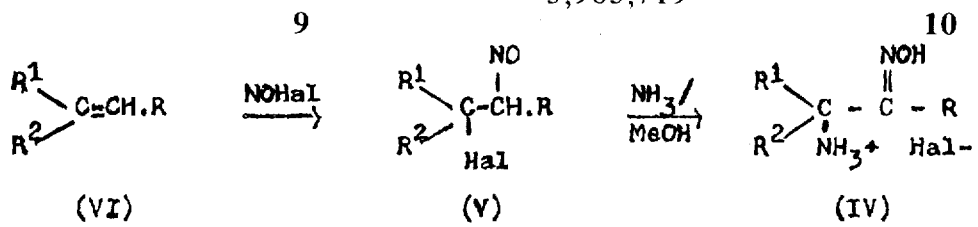
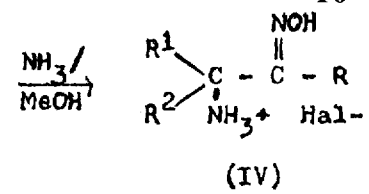

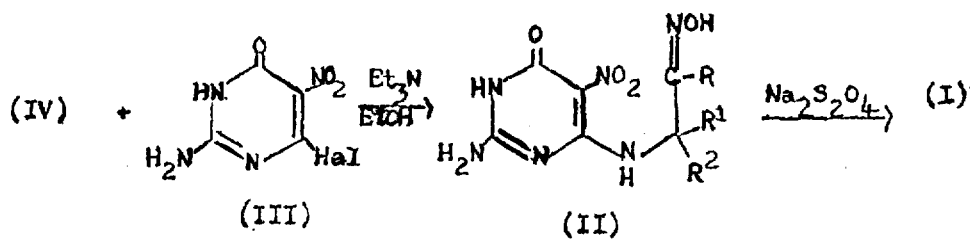

The compound of formula (VI) wherein R is a hydroxyalkyl group may in turn be prepared from the ketone $R^1R^2C=O$ (IX) by reacting this with a trialkylphosphonoester (VIII) and reducing the ester (VII) so formed to give the alcohol (VI).

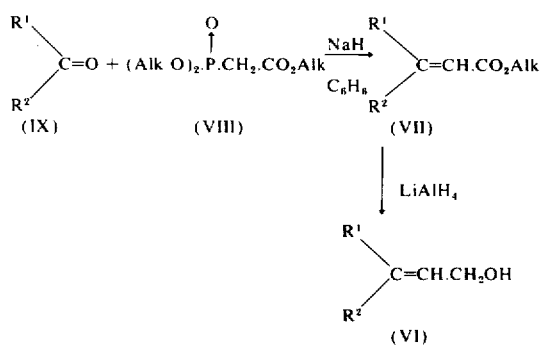

If a pteridine having $R^1$ and $R^2$ as different substituents is required, then a racemic mixture of two stereoisomers of the nitrosohalide (V) will be obtained in view of the asymmetric carbon atom present. Separation of the two isomers by conventional techniques known in the art at this stage may be advantageous.

According to the present invention in further aspects there are also provided:

1. The methods described herein for preparing any of the compounds of formula (I), comprising effecting reductive cyclisation of the compounds of formula (II).

2. The methods described herein for preparing any of the compounds (II), wherein Z is an oxime group, from (IV), (IV) from (V) or (VI) and (VI) from (IX).

3. Compounds of formula (I), (II), wherein Z is an oxime group, (IV) and (V), whenever prepared by a method as defined under (1) or (2).

4. As novel compounds of value as chemical intermediates: compounds of formula (II), (IV) and (V).

5. A pharmaceutical formulation comprising a compound of formula (I) or a salt thereof in combination with a pharmaceutically acceptable carrier, whenever prepared by the method herein described.

The following Examples illustrated the invention but are in no way intended to limit the scope of the invention.

Temperature are in degrees Celsius.

EXAMPLE A

Preparation of 2-amino-4-hydroxy-6-hydroxymethyl-7,7-diethyl-7,8-dihydropteridine. (I, R=$CH_2$OH; $R^1$=$R^2$=Et)

EXAMPLE 1

Ethyl 3-ethylpent-2-enoate (VII) ($R^1$=$R^2$=Et)

Sodium hydride (6 g) was placed in a flask with sodium dried benzene (100 ml) and the flask was flushed with oxygen-free dry nitrogen. To this solution was added a slight excess of triethylphosphonoacetate (VIII) (Alk=Et) (61.7 g) over a period of 1.5 h and the temperature was maintained <15° during the addition. The mixture was stirred at this temperature for an additional 1 h and then treated dropwise with pentan-3-one (IX), ($R^1$=$R^2$=Et) (21.5 g). After addition of the ketone was complete the reaction mixture was stirred at room temperature until the solid sodium diethyl phosphate had precipitated (approx. 10 h). The mother liquor was decanted from the solid, which was washed with benzene (4 × 25 ml). The benzene extracts were combined and evaporated in vacuo to give a pale yellow oil (29 g) which was distilled in vacuo to give ethyl 3-ethylpent-2-enoate (VII) (21.8 g, yield 56%) as a colourless oil, b.p. 52°–54°/4 mm. Hg.

EXAMPLE 2(a)

3-Ethylpent-2-en-1-ol.(VI) ($R^1$=$R^2$=Et)

Ethyl 3-ethylpent-2-enoate (VII) (42.3 g) in dry ether (400 ml) was treated dropwise with a 70% solution (in benzene) of a slight excess of sodium dihydro bis ethoxymethoxy aluminate (S.D.A.) (86.1 g), the temperature being maintained at 0° until the addition of the reducing agent was complete. The reaction mixture was then stirred at room temperature for 6 h and the excess S.D.A. was destroyed by the careful addition of water. The solid sodium aluminate which precipitated was filtered off and the filtrate extracted with ethyl acetate (4×50 ml). The combined extracts were washed with brine, dried over sodium sulphate and the solvent removed. The resulting pale yellow oil (23 g) was distilled to give 3-ethylpent-2-en-1-ol (VI) (18.5 g, yield 60%) as a colourless viscous oil b.p. 60°/4 mm. Hg.

EXAMPLES 2(b)

3-Ethylpent-2-en-1-ol (VI) ($R^1$=$R^2$=Et)

A slurry of lithium aluminium hydride (L.A.H.) (8.2 g) in dry ether was added dropwise to a solution of ethyl 3-ethylpent-2-enoate (VII) (33.7 g) in dry ether (100 ml) at 0°. After the addition of the L.A.H. was complete the mixture was stirred at room temperature for 2 h. The excess L.A.H. was destroyed at 0° by adding a saturated solution of sodium sulphate. The solution was filtered and the filtrate extracted with ethyl acetate and worked up as described in Example 2(a) to give the alcohol (VI) (19 g, yield 77%).

EXAMPLE 3

3chloro-3-ethyl-2-nitroso-pentan-1-ol. (V) ($R=CH_2OH$; $R^1=R^2=Et$)

Concentrated hydrochloric acid (23 ml) was added dropwise over 1.5 h to a mixture of 3-ethylpent-3-en-1-ol (VI) (23 g) and amyl nitrite (22.4 g) in glacial acetic acid (46 ml) at 0° (ice-salt bath). After the addition of the acid was complete the mixture was stirred at this temperature for 30 min, then cooled in an acetone-carbon dioxide bath for 15 min when a white paste formed. The solid was filtered off, washed with water and cold methanol and recrystallised from benzene to give the nitrochloride (V) (13 g, yield 36%) as colourless crystals, m.p. 110°.

EXAMPLE 4

3-Amino-3-ethyl-1-hydroxy-pentan-2-one oxime hydrochloride (VI) ($R=CH_2OH$; $R^1=R^2=Et$)

3-Chloro-3-ethyl-2-nitroso-pentan-1-ol (V) (10 g) was placed in a three-necked round-bottomed flask and treated with a saturated solution of ammonia in methanol. The flask was stoppered, each stopper being secured with copper wire, and the mixture was stirred at room temperature for 2days. A clear yellow solution was obtained. The solvent was removed in vacuo at room temperature and the yellow oil obtained was triturated with hot benzene and the benzene decanted. The residue was dissolved in ethanol and the insoluble ammonium chloride present was filtered off. The ethanol was removed in vacuo at room temperature and the residual yellow oil was treated with hot acetone to give a white solid which was filtered off, washed with acetone and recrystallised from butan-2-ol to give the ketoxime hydrochloride (VI) (5 g; yield 46%) as colourless needles, M.Pt. 182°–184°.

EXAMPLE 5

2-Amino-4-hydroxy-6(1,1-diethyl-3-hydroxy-2-hydroxyiminopropylamino)-5-nitropyrimidine (II) ($R=CH_2OH$; $R^1=R^2=Et$) $1=R^2=Et$)

A suspension of 2-amino-4-chloro-6-hydroxy-5-nitropyrimidine (III) (Hal=Cl) (2.6 g) in dry ethanol (50 ml) was treated with 3-amino-3-ethyl-1-hydroxy-pentan-2-one oxime hydrochloride (VI) (2.66 g) and dry triethylamine (2.89 g) and the mixture was refluxed for 8 h. The solution was filtered and the filtrate evaporated to dryness in vacuo at room temperature. The yellow oil obtained was treated with cold water and the yellow solid which precipitated was filtered off and washed with water. Recrystallisation from water in the presence of charcoal gave the nitropyrimidine oxime (II) (1.3 g; yield 30%) as a fine white solid m.p. <250° (decomp.).

EXAMPLE 6

2-Amino-4-hydroxy-6-hydroxymethyl-7,7-diethyl-7,8-dihydropteridine (I) ($R=CH_2OH$; $R^1=R^2=Et$)

Sodium dithionite was added portionwise to a warm solution of 2-amino-4-hydroxy-6-(1,1-diethyl-3-hydroxy-2-hydroxyiminopropylamino)-5-nitropyrimidine (II) (450 mg) in 0.1M sodium hydroxide until the colour changed from red to very pale yellow. A solid product was not obtained either on cooling or on adjusting the pH. In order to separate the product from inorganic material the solution was evaporated and the product extracted with ethanol and the inorganic material was filtered off. This extraction was repeated and the combined extracts were evaporated to dryness in vacuo. The residue was dissolved in the minimum quantity of water and placed on a column of Amberlite (C.G.50) ion exchange resin (2.5 × 28 cm). Elution with water gave two main fluorescent bands. Evaporation of the solution containing the first band gave the 6-carboxaldehyde derivative of the title compound (10 mg, yield 3%) as a bright orange powder, whilst the second band gave the 7,8-dihydropteridine (I) (160 mg, yield 44.5%) as a bright yellow powder, m.p. <300° decomp.

EXAMPLE B

Preparation of 2-Amino-4-hydroxy-6-hydroxymethyl-7-spirocyclohexyl-7,8-dihydropteridine (I) ($R=CH_2OH$; $R^1R^2=$spirocyclohexyl).

EXAMPLE 1

Ethyl cyclohexylidene acetate (VII) ($R^1R^2=$spirocyclohexyl).

Sodium dried benzene (200 ml) was added to a flask containing sodium hydride (16 g) and the flask was flushed with oxygen-free dry nitrogen. To this mixture was added, over 1 h, a slight excess of triethylphosphonoacetate (VIII) (Alk=Et) (164.3 g) keeping the temperature at 0°. The reaction mixture was stirred for an additional hour at 0° and then treated with cyclohexanone (IX) ($R^1R^2=$spirocyclohexyl) (65.4 g) at the same temperature.

After the addition of the cyclohexanone was complete (≈40 min) the mixture was stirred at room temperature for 3 h; stirring became difficult after this time due to a gummy precipitate of sodium diethyl phosphate.

The mixture was then heated at 60°–65° for 15 min during which time it was stirred without difficulty. The mixture was cooled to 15° and the benzene solution was decanted and the solid washed with benzene. THe combined mother liquor and washings were evaporated to give a pale yellow oil which on distillation gave ethyl cyclohexylidene acetate (VII) (62 g; yield 55.4%) as a colourless oil, b.p. 86°–88°/2 mm. Hg

EXAMPLE 2(a)

2-Cyclohexylidene ethanol (VI) ($R^1R^2=$spirocyclohexyl)

A 70% solution (in benzene) of sodium dihydrobisethoxymethoxy aluminate (100g) was added portionwise to ethyl cyclohexylidene acetate (VII) (58.8 g) in dry ether (300 ml) at 0°. The reaction mixture was stirred for 6h at room temperature and the excess reducing agent was destroyed by the addition of water. The solid sodium aluminate was filtered off and the filtrate extracted with ethyl acetate (4 × 50 ml). The combined extracts were washed with brine, dried over sodium sulphate and the solvent evaporated in vacuo. A pale yellow oil was obtained which on distillation gave 2-cyclohexylidene ethanol (VI) (31 g; yield 70%) as a colourless oil, b.p. 80°/2mm Hg.

Example 2(b)

2-Cyclohexylidene ethanol (VI) ($R^1R^2$=spirocyclohexyl)

A solution of ethyl cyclohexylidene acetate (VII) (60 g) in dry ether (300ml) was cooled to 0° and treated portionwise with a slurry of lithium aluminium hydride (15 g) in dry ether (150 ml), the temperature being kept below 5° during the addition. The reaction mixture was stirred for 15 min at this temperature and for an additional 20 min at room temperature. The excess hydride was destroyed with saturated sodium sulphate and the ethereal solution worked up as above to give the alcohol (VI) (23 g; yield 51%) as a colourless oil.

EXAMPLE 3

3-Chloro-2-nitroso-3-spirocyclohexylpropan-1-ol (V) ($R$=$CH_2OH$; $R^1R^2$=spirocyclohexyl).

2-Cyclohexylidene ethanol (VI) (23 g) was dissolved in glacial acetic acid (76 ml). Amyl nitrite (21.5 g) was added and the mixture was cooled in an ice-salt bath. The cooled solution was treated dropwise with cold concentrated hydrochloric acid (23 ml) with stirring. After the addition of the acid was complete the reaction mixture was stirred at the same temperature for 30 min, followed by cooling in an acetone-carbon dioxide bath for 10 min. The buff-coloured solid was filtered off, washed with cold methanol and recrystallised from acetone to give the nitrosochloride (V) (15 g; yield 43%) as colourless needles, m.p. 130°.

EXAMPLE 4

3-Amino-1-hydroxy-3-spirocyclohexylpropan-2-one oxime hydrochloride (VI) ($R$=$CH_2OH$; $R^1R^2$=spirocyclohexyl A solution of methanol saturated with ammonia was added to 3-chloro-2-nitroso-3-spirocyclohexylpropan-1-ol (V) (14.5 g) in a tightly secured stoppered flask and the mixture was stirred for three days at room temperature. The reaction mixture was then refluxed for 1.5 h in an atmosphere of ammonia, cooled and filtered. The solvent was removed and the residual yellow oil washed with hot benzene and decanted. The solid was recrystallised from ethanol giving the oxime hydrochloride (IV) (7.8 g; yield 50%) as colourless crystals, M.Pt. 197°.

EXAMPLE 5

2-Amino-4-hydroxy-6-(3-hydroxy-2-hydroxyimino-1-spirocyclohexylpropylamino)-5-nitropyrimidine (II) ($R$=$CH_2OH$; $R^1R^2$=spirocyclohexyl)

A suspension of 2-amino-4-chloro-6-hydroxy-5-nitropyrimidine (III) (Hal=Cl) (2.3 g) in dry ethanol was treated with 3-amino-1-hydroxy-3-spirocyclohexylpropan-2-one oxime hydrochloride (IV) (2.5g) and dry triethylamine (2.7 g) and the mixture was refluxed for 7 h. The reaction mixture was filtered and the solid washed with hot ethanol. The solvent was removed from the filtrate and the resulting yellow oil was triturated with cold water giving a yellow solid which on recrystallisation from water in the presence of charcoal gave the nitropyrimidine (II) (1.85 g; yield 47.4%) as an off-white powder, m.pt <300° (decomp.).

EXAMPLE 6

2-Amino-4-hydroxy-6-hydroxymethyl-7-spirocyclohexyl-7,8-dihydropteridine (I) ($R$=$CH_2OH$; ($R^1R^2$=spirocyclohexyl).

2-Amino-4-hydroxy-6-(3-hydroxy-2-hydroxyimino-1-spirocyclohexylpropylamino)-5-nitropyrimidine (II) (500 mg) was dissolved in the minimum of 0.1M sodium hydroxide by warming on the steam bath. Sodium dithionite was added portionwise until an almost colourless solution was obtained. On cooling the dihydropteridine separated and was filtered off and purified by dissolving in 2M HCl and reprecipitated by the addition of 0.88 ammonia to pH8. On standing the dihydropteridine (I) (150 mg; yield 38%) was obtained as a pale yellow crystalline solid, m.p. <300 (decomp.).

EXAMPLE C

Potential pteridine antagonists of formula (I) may be tested by investigating the inhibitory effect they impose on the enzymes responsible for the biosynthesis of dihydropteroic acid (DPtA), namely hydroxymethyldihydropteridine pyrophosphokinase (HMPPS), and dihydropteroate synthetase, hereinafter referred to as 'synthetase'. In the following reaction equations the compounds are referred to by their abbreviated forms defined on page 5 of the specification.

1. HMPPS

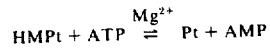

2. Synthetase

a. An assay for HMPPS was developed in which the transfer of the terminal phosphate of ATP-γ-$p^{32}$ to Pt could be monitored and correlated with the amount of inhibition of HMPPS by the compound under test.

The compound of formula (I) which was under test was incorporated into various formulations comprising metabolites and enzymes contained in test tubes, as indicated in TABLE 1.

The components of the mixture were as follows:
 I. 2-amino-4-hydroxy-6-hydroxymethyl-7,8-dihydropteridine (HMPt) in a concentration of 800 μM i.e. micromolar;
 II. a source of HMPPS, obtained from an extract of E. coli and separated from 'synthetase' on sephadex G-100, (Registered Trade Mark) according to the method of Richey and Brown in *J.Biol.Chem*.244, 1582–1592 (1969)
 III. 3mM ATP -γ-$P^{32}$.
 IV. 0.10 M ATP neutralised (unlabelled).
 V. 0.02M $MgCl_2$. $6H_2O$.
 VI 0.1 M $MgCl_2.6H_2O$.
 VII Source of HMPPS and 'synthetase'
 VIII the test compound in a concentration of 0.93×$10^{-3}$ M
 IX 0.4mM pAB-$C^{14}$ As shown in TABLE 1, tubes 1 to 9 all contain a source of HMPPS, labelled ATP and 0.02 M $MgCl_2.6H_2O$, tubes 2 to 9 containing in addition HMPt and tubes 4 to 9 further containing the test compound.

Control tubes 10 to 12 include a source of both HMPPS and synthetase, unlabelled ATP, 0.1M MgCl$_2$.6H$_2$O and labelled pAB.

Tubes 1 to 9 containing the amounts of components shown in the Table, were filled up to 200μl with distilled water, incubated for 60 minutes at 37°C and then chilled on ice. Dextrose (20μl containing 72.1 mg/ml) and hexokinase (5μl containing 2000 units/ml) were added to the solution, which was then allowed to stand at room temperature for 15 minutes. 'Darco-G-60' (Registered Trade Mark) (10 mg) was added to each tube and the contents mixed periodically for 10 minutes. The charcoal was removed through a 'Millipore AP 250 2200' (Registered Trade Mark) filter and the filter was washed with three 10 ml portions of cold water. The charcoal and the filter were then radioactively counted.

The radioactive count from the contents of tubes 2 and 3 was taken as the maximum count, since these tubes contained no test compound and thus gave 0% enzyme inhibition. The percentage inhibition produced by the contents of the remaining tubes could then be calculated by relating their radioactive count to the maximum, as determined above.

The contents of tubes 10 to 12 were chromatographically analysed as described under part (b), and used as controls, tubes 10 and 11 containing no test compound (and hence giving 0% inhibition) being accorded the value of 100%. The percentage inhibition exhibited by the contents of the tubes in part (b) of the experiment could then be calculated in relation to this, by comparing the respective chromatograms. (b) The activity of the test compound of formula (I) against 'synthetase' was determined as follows, by monitoring the formation of dihydropteroate C$^{14}$.

A pool of Pt was prepared from ATP neutralised (50μl, 0.1M), MgCl$_2$.6H$_2$O(50μl,0.1M), dithiothreitol (100μl,0.1M), tris buffer (100μl,0.4M,pH 8.3), HMPt (25μl,876μM) and 170μl of a solution containing HMPPS. The mixture was incubated for 60 minutes at 37°C, chilled briefly on ice and then dextrose (100μl containing 72.1mg/ml and hexokinase (20μl containing 2000 units/ml) were added at room temperature to the solution, which was allowed to stand at this temperature for 15 minutes.

A solution of MgCl$_2$.6H$_2$O (10μl,0.1M), pAB-C$^{14}$ (10μl,0.4mM), dithiothreitol (20μl,0.1M) and tris buffer (20μl,0.4M,pH8.3) was made in each of five test tubes and then 80μl of the contents of the pool added to each, together with synthetase and/or test compound of formula (I) as indicated in Table 2. The solution was then made up to 200μl with distilled water.

Two control test tubes were prepared, each containing ATP (10μl,0.1M), MgCl$_2$.6H$_2$O(10μl,0.1M), dithiothreitol (20μl,0.1M) tris buffer (20μl,0.4M,pH 8.3), pAB-C$^{14}$ (10μl,0.4mM), and 20μl of a solution containing HMPPS and 'synthetase' of known activity. The test compound was added to the second of these two tubes up to a final concentration of 10$^{-5}$M, and both tubes were made up with distilled water to 200μl.

All seven tubes were then incubated for 30 minutes at 37°C, chilled on ice and then these, together with control tubes 10 to 12 from part (a), were chromatographically analysed as follows.

100μl of the contents of each of the tubes was spotted onto Whatman no. 3MM chromatography paper (2×20 cm) at the 'origin', the run descending in a Sorenson buffer of potassium and sodium phosphates (0.1M,pH 7.0) for 10 to 15 cm. From the relative positions of the spots obtained from the contents of the different tubes, the various percentage inhibitions of synthetase could be evaluated by reference to control tubes 10 and 11, which gave 0% inhibition.

Those compounds which, as result of these tests, were found to give 50% inhibition at a concentration of 100μM or less, are those which exert a useful potentiating effect, and subject to their toxicity being favourable, may be included in the compositions described in this specification.

2-Amino-4-hydroxy-6-hydroxymethyl-7,7-diethyl-7,8-dihydropteridine was found to give 50% inhibition at a concentration of 2.1μM.

EXAMPLE D

In this experiment inhibitor zone data were determined to evaluate the synergistic activity of 2-amino-4-hydroxy-6-hydroxymethyl-7,7-diethyl-7,8-dihydropteridine on its combination with trimethoprim (TMP) and/or sulphamethoxazole (SMX) against *Staphylococcus aureus*.

The pteridine was included in a soya peptone medium of low thymidine content (Wellcotest Sensitivity test agar) contained in a Petri dish and the other component(s) added to the well resulting from the removal of a small plug from the medium. The surface of the medium was inoculated with the test organism and then incubated. The amount of zone inhibition is shown in Table 3, wherein the numbers represent the complete zone inhibition (i.e. the number of centimeters from the edge of the well after about 6 × magnification) and the figures in parenthesis include the zones of partial inhibition.

The Results show that the pteridine shows synergism with TMP and SMX alone and multiple synergism with both against *Staphylococcus aureus*.

Example E

Tablet Formulation
| | |
|---|---|
| Compound of formula (I)(R=CH$_2$OH;R$^1$=R$^2$=Et) (pure) | 100 mg |
| Trimethoprim (pure) | 25 mg |
| Sulfaguanidine (B.P.C.) | 100 mg |
| + cornstarch, lactose, gelatin, talcum and magnesium stearate | |

Preparation

The above constituents were mixed together using known methods of pharmacy to form a granulation which was then compressed into tablets.

Example F

Tablet Formulation
| | |
|---|---|
| "Pyremathimine" (Pyrimethamine) B.P. | 15 mg |
| Compound of forumua (I)(R=CH$_2$OH;R$^1$=R$^2$=Et) (pure) which was then prepared to form a tablet as in Example E. | 150 mg |

Example G

Tablet Formulation
| | |
|---|---|
| Sulfanilamide B.P.C. | 150 mg |
| Compound of formula (I)(R=CH$_2$OH;R$^1$=R$^2$=Et) (pure) which was then prepared to form a tablet as in Example E. | 175 mg |

Example H

Capsule Formulation
| | |
|---|---|
| Trimethoprim (pure) | 20 mg |
| Compound of formula (I)(R=CH$_2$OH;R$^1$=R$^2$Et) (pure) | 100 mg |

Preparation

The compounds in granular form were blended together with lactose, cornstarch and magnesium stea-

Example I

| Irrigant Solution | |
|---|---|
| Compund of formula (I)(R=CH₂OH;R¹=R²=Et) (pure) | 1 mg/ml |
| Trimethoprim (pure) | 0.2 mg/ml |
| Solvent | water |

Example J

| Irrigant Solution | |
|---|---|
| Compound of formula (I)(R=CH₂OH;R¹=R²=Et) | 2 mg/ml |
| α-amino-p-toluenesulphonamide (pure) | 2 mg/ml |

EXAMPLE K

| Solution | |
|---|---|
| Compound of formula (I)(R=CH₂OH;R¹=R²=Et) (pure) | 1.5 mg/ml |
| Diaveridine B. Vet C | 0.5 mg/ml |
| Kelfizina | 1.0 mg/ml |
| Solvent | water |

Example L

| Tablet Formulation | |
|---|---|
| Compound of formula (I)(R=CH₂OH;R¹=R²=Et) (pure) | 500 mg |
| Microcrystalline cellulose | 100 mg |
| Starch | 40 mg |
| Magnesium stearate | 10 mg |
| Methylhydroxyethylcellulose | 3 mg |
| | 653 mg |

The pteridine (I), microcrystalline cellulose and starch were granulated with a solution of the methylhydroxyethylcellulose in 50% aqueous ethyl alcohol. The magnesium stearate was added to the dried granules, and the whole then compressed.

TABLE 1

| Tube No. | I | II | III | IV | V | VI | VII | VIII Final Concn. | IX |
|---|---|---|---|---|---|---|---|---|---|
| 1 | — | 100µl | 15µl | — | 10µl | — | — | — | — |
| 2 | 5µl | ″ | ″ | — | ″ | — | — | — | — |
| 3 | ″ | ″ | ″ | — | ″ | — | — | — | — |
| 4 | ″ | ″ | ″ | — | ″ | — | — | 2.5×10⁻⁶M | — |
| 5 | ″ | ″ | ″ | — | ″ | — | — | ″ | — |
| 6 | ″ | ″ | ″ | — | ″ | — | — | 1.0×10⁻⁵M | — |
| 7 | ″ | ″ | ″ | — | ″ | — | — | ″ | — |
| 8 | ″ | ″ | ″ | — | ″ | — | — | 9.3×10⁻⁵M | — |
| 9 | ″ | ″ | ″ | — | ″ | — | — | ″ | — |
| Controls | | | | | | | | | |
| 10 | — | — | — | 10µl | — | 10µl | 20µl | | 10µl |
| 11 | 5µl | — | — | ″ | — | ″ | ″ | | ″ |
| 12 | ″ | — | — | ″ | — | ″ | ″ | 1.0×10⁻⁵M | ″ |

TABLE 2

| Tube No. | Excess Synthetase | Test compound Final Concentration. |
|---|---|---|
| 1 | — | — |
| 2 | + | — |
| 3 | + | 8.7×10⁻⁵M |
| 4 | + | 1.0×10⁻⁵M |
| 5 | + | 2.5×10⁻⁶M |
| Controls | | |
| 6 | — | — |
| 7 | — | 1.0×10⁻⁵M |

TABLE 3

| Drug (µg/ml) | Staphylococcus aureus | | |
|---|---|---|---|
| | TMP (30) | SMX (300) | TMP + SMX (5) (100) |
| R=CH₂OH R¹=R²=Et (30) | 12.5(17.0) | 12.5(17.0) | 12.5(17.0) |
| ″ (10) | 10.5(13.0) | 10.5(14.0) | 11.0(14.5) |
| ″ (3) | 8.5(10.5) | 6.5(12.5) | 10.5(12.5) |

What we claim is:

1. A compound of the formula, or a tautomeric form thereof

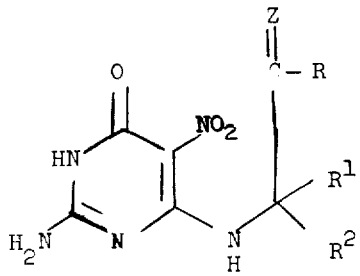

wherein Z is oxygen or a protecting group therefore, R is lower alkyl or hydroxylower alkyl, and R¹ and R², having in total 4 to 6 carbon atoms, form a spirocycloalkyl group together with the carbon atom substituted by said R¹ and R².

2. The compound according to claim 1, which is 2-Amino-4-hydroxy-6-(3-hydroxy-2-hydroxyimino-1-spirocyclohexylpropylamino)-5-nitropyrimidine.

* * * * *